(12) United States Patent
Rodriguez et al.

(10) Patent No.: US 8,209,031 B1
(45) Date of Patent: Jun. 26, 2012

(54) IMPLANTABLE LEAD FOR MEASURING PHYSIOLOGIC INFORMATION

(75) Inventors: Rodolfo Rodriguez, Santa Monica, CA (US); Annapurna Karicherla, Valencia, CA (US)

(73) Assignee: Pacesetter, Inc., Sylmar, CA (US)

(*) Notice: Subject to any disclaimer, the term of this patent is extended or adjusted under 35 U.S.C. 154(b) by 753 days.

(21) Appl. No.: 11/696,962

(22) Filed: Apr. 5, 2007

(51) Int. Cl.
*A61N 1/05* (2006.01)

(52) U.S. Cl. ........... 607/116; 607/17; 607/115; 607/119

(58) Field of Classification Search .............. 607/7, 23, 607/116, 119, 17, 115
See application file for complete search history.

(56) References Cited

U.S. PATENT DOCUMENTS

| | | | |
|---|---|---|---|
| 4,600,017 A * | 7/1986 | Schroeppel | 607/122 |
| 5,261,418 A | 11/1993 | Ferek-Petric | |
| 5,271,392 A | 12/1993 | Ferek-Petric | |
| 5,899,927 A * | 5/1999 | Ecker et al. | 607/23 |
| 2005/0209649 A1 | 9/2005 | Ferek-petric | |
| 2006/0119224 A1* | 6/2006 | Keolian et al. | 310/339 |

FOREIGN PATENT DOCUMENTS

| | | |
|---|---|---|
| EP | 0473070 | 3/1992 |
| WO | WO02/28478 | 4/2002 |

* cited by examiner

*Primary Examiner* — Carl H Layno
*Assistant Examiner* — Pamela M Bays

(57) ABSTRACT

An implantable lead includes a lead body, having a distal end and a proximal end, configured to be implanted in a patient, and a connector provided at the proximal end. A load detection assembly is provided on the lead body, wherein the load detection assembly includes a housing that holds a sensor and a load transfer element. The load transfer element engages the sensor and conveys a force induced on the load transfer element to the sensor. Optionally, the housing may isolate the sensor from lateral forces and the load transfer element may only convey, to the sensor, longitudinal forces that are directed in a predetermined single direction. For example, the load transfer element may only convey, to the sensor, longitudinal forces that are directed perpendicular to a surface of the sensor.

15 Claims, 6 Drawing Sheets

IMPLANTABLE LEAD FOR MEASURING PHYSIOLOGIC INFORMATION

BACKGROUND OF THE INVENTION

The various embodiments described herein generally relate to implantable leads, and more particularly to implantable leads used for measuring pressure of fluids or tissues within a patient's body.

Pressure tracking of fluids or tissue within a patient's body is useful for predicting pathological conditions of the patient. For example, coronary pressure tracking of the blood within the heart and/or the heart tissue is useful for predicting heart diseases that may lead to heart failure. Several types of pressure sensors, used in connection with an implantable medical device (IMD), have been used to measure coronary pressure.

One known type of pressure sensor utilizes strain gauges to measure pressure. These known sensors include wires that are adhered to a surface of the heart. An electrical potential is maintained across the wires and a change in resistance of the wires is measured. The change in resistance correlates to an amount of extension of the wires and translates to the forces acting on the surface, because the amount of extension is based on an amount of deflection of the surface. However, a major drawback to using strain gauges to measure coronary pressure is that the strain gauge requires that an electrical potential be maintained across the wires, which consumes battery life of the IMD.

Another known type of pressure sensor utilizes a piezoelectric sensor to measure pressure. Some known piezoelectric sensors include a piezoelectric strip located at a bend of a J-shaped pacing lead that is implantable in the atrium or ventricle. The piezoelectric strip extends longitudinally along the lead and measures movement of the lead at the bend. Other known piezoelectric sensors include piezoelectric strips that are disposed on a surface of a patch electrode that is adhered to an outer surface of the heart. The piezoelectric sensor measures expansion and contraction of the heart surface. However, one drawback to using the piezoelectric strip to measure coronary pressure occurs because the piezoelectric sensors detect many different forces at the same time, such as lateral forces, shear forces, bending forces and rotational forces. Because many different forces are simultaneously detected, the voltage transmitted by the piezoelectric sensor may be inaccurate. Another drawback to using the piezoelectric strips to measure coronary pressure is that the voltage generated by the piezoelectric sensor typically have a very low signal to noise ratio. One way in which known piezoelectric sensors overcome this problem is to increase the surface area of the piezoelectric strip, thus increasing the overall size of the IMD.

SUMMARY

In accordance with one embodiment, an implantable lead is provided including a lead body, having a distal end and a proximal end, configured to be implanted in a patient, and a connector provided at the proximal end. A load detection assembly is provided on the lead body, wherein the load detection assembly includes a housing that holds a sensor and a load transfer element. The load transfer element engages the sensor and conveys a force induced on the load transfer element to the sensor.

Optionally, the housing may isolate the sensor from lateral forces and the load transfer element may only convey, to the sensor, longitudinal forces that are directed in a predetermined single direction. For example, the load transfer element may only convey, to the sensor, longitudinal forces that are directed perpendicular to a surface of the sensor. Optionally, the housing may include an interior chamber that holds and isolates the sensor from a surrounding environment. The interior chamber may be exposed through an opening in the housing to incident forces of a surrounding environment directed perpendicular to the opening. The load transfer element may have a first end that directly engages a surface of the sensor and a second end that is exposed to a surrounding environment. Optionally, the load transfer element may be one of a spring, a deflectable solid polymer, a gel and a liquid filled pouch.

In accordance with one embodiment, an implantable lead is provided including a lead body, having a distal end and a proximal end, configured to be implanted in a patient, and a connector provided at the proximal end. A load detection assembly is provided on the lead body, wherein the load detection assembly includes multiple piezoelectric sensors arranged in-line with one another along a common longitudinal axis. The piezoelectric sensors cooperate with one another such that a force induced onto one of the piezoelectric sensors is experienced by the other piezoelectric sensors.

DETAILED DESCRIPTION

Figure 1:
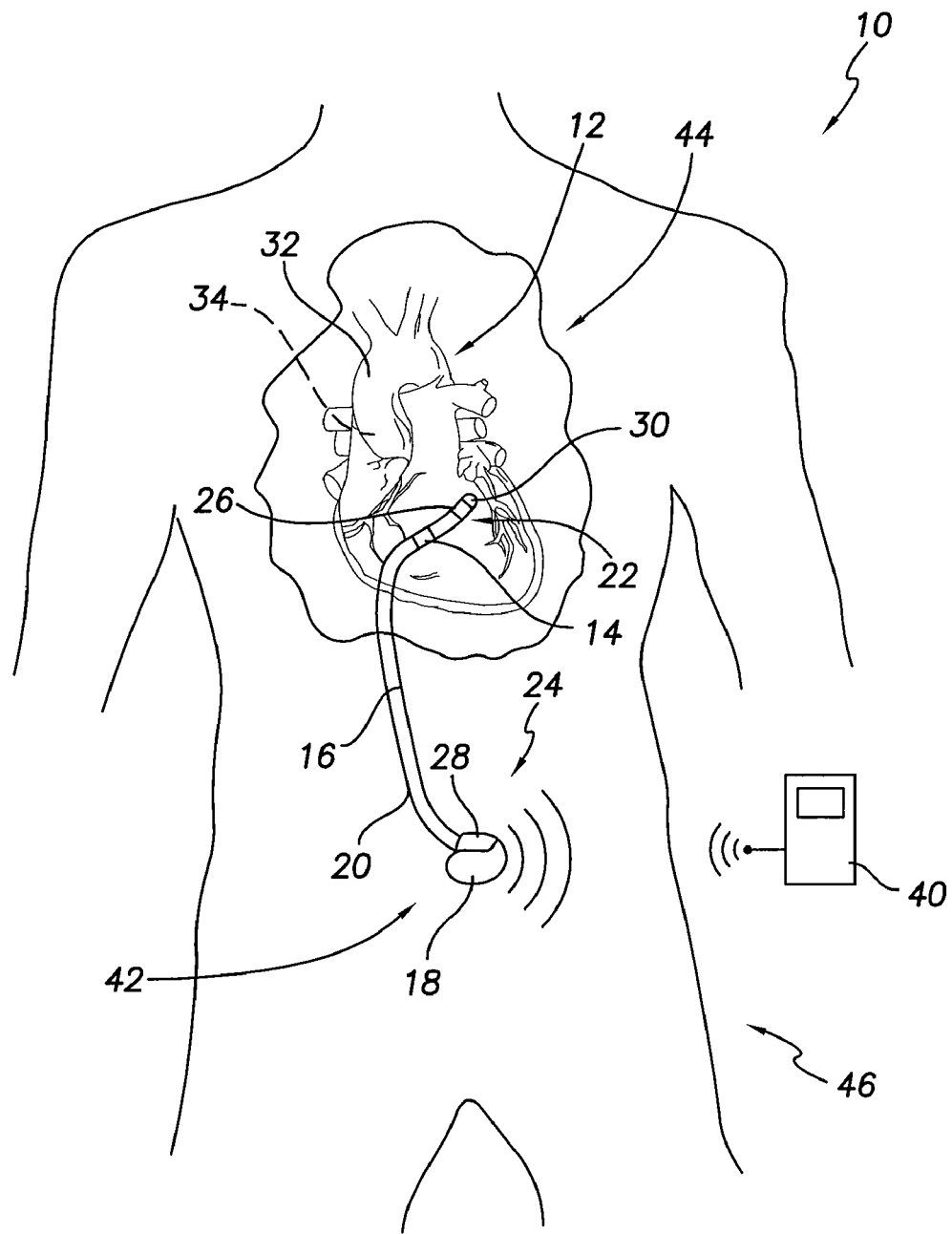
FIG. 1 illustrates an implantable sensor system formed in accordance with an exemplary embodiment.

FIG. 1 illustrates an implantable sensor system 10 formed in accordance with an exemplary embodiment. The sensor system 10 may be used, for example, for generally monitoring a physiological condition of a patient's heart 12, e.g., monitoring cardiac pressure or motion. The system 10 includes a load detection assembly 14, an attachment device 16 for positioning the load detection assembly 14 in direct contact with bodily tissue and/or bodily fluid, and a processing unit 18. The attachment device 16 is generally illustrated in the Figures and described hereinafter as a lead 16, however, other types of devices may be used for positioning the load detection assembly 14. The processing unit 18 is generally illustrated in the Figures as a therapy delivery module, such as a pulse generator, a pacemaker, an implantable cardioverter defibrillator, a defibrillator, and the like. As will be described in more detail below, the load detection assembly 14 detects or senses a force or pressure, in response to motion of the bodily tissue and/or bodily fluid in the environment surrounding the load detection assembly 14. An electrical charge is generated by the load detection assembly 14, and a voltage of the electrical charge is proportional to the amount of pressure sensed by the load detection assembly 14. Voltage measurement signals are processed by the processing unit 18 and used to determine motion properties of the fluid and/or tissue whose motion was detected by the load detection assembly 14.

The lead 16 includes a lead body 20 having a distal end portion 22 and a proximal end portion 24. The lead body 20 has a length that extends along a longitudinal axis between the distal and proximal end portions 22 and 24. The term longitudinal axis encompasses both linear and non-linear axes. The longitudinal axis of the lead body 20 extends along a curved path that changes as the lead body is flexed, bent and otherwise manipulated. The lead 16 may include at least one electrode 26, in addition to the load detection assembly 14, in the form of a ring electrode and/or a tip electrode. The lead body 20 includes an insulating sheath or housing of a suitable insulative, biocompatible, biostable material such as, for example, silicone rubber or polyurethane, extending substantially the entire length of the lead body 20. Optionally, the lead 16 may include a connector 28 at the proximal end portion 24 for connecting to the processing unit 18. The lead 16 may include, along the distal end portion 22, a plurality of projecting tines 30 that function to interlock the lead 16 within the tissue and thereby prevent inadvertent displacement of the distal end portion 22 once the lead 16 is implanted. While the tines 30 represent one type of attachment means, optionally other attachment means may be utilized and the attachment means may include any suitable structures, elements, components, configurations, arrangements, and/or geometries that securely position and hold the load detection assembly 14 in the positions (e.g., location and/or orientation) described and/or illustrated herein. For example, the attachment means may constitute fins, a screw-in helix, or some other suitable attachment means may be used instead, including one or more S-shaped bends along the distal end portion, without tines, for anchoring. Alternatively, the tines 30 and all other attachment means may be removed entirely.

In the illustrated embodiment of FIG. 1, the load detection assembly 14 is coupled to the lead 16 remote from the distal end portion 22. As such, at least a portion of the lead 16 extends beyond the load detection assembly 14. The portion extending beyond the load detection assembly 14 may include the pacing and/or sensing electrode 26. The load detection assembly 14 is housed within the lead 16 such that a portion of the load detection assembly 14 is exposed to the environment surrounding the lead 16. The lead 16 operates to position the load detection assembly 14 within and/or adjacent the heart 12 for obtaining pressure information about the heart 12. However, the sensor system 10 is not limited to use with the heart 12, but rather may be used to measure the motion of any bodily tissue and/or bodily fluid, such as, but not limited to, joints, the brain, the lungs, the stomach, and/or other muscles or organs within the body besides the heart 12.

When used to measure the pressure of the heart 12, the load detection assembly 14 may be positioned anywhere within, on, and/or adjacent the heart 12 that is suitable for measuring motion of the heart 12 itself and/or blood being pumped through the heart 12. For example, the load detection assembly 14 may be positioned in the pericardial space in direct contact with an epicardial, or external, surface 32 of the heart 12, as is shown in FIG. 1, wherein the load detection assembly 14 is positioned on an epicardial surface 32 of a left ventricle of the heart 12. In alternative embodiments, such as in the embodiment illustrated in FIG. 2, the load detection assembly 14 may be positioned in direct contact with an endocardial, or internal, surface 34 of the heart 12, e.g., an endocardial surface of the left ventricle. The load detection assembly 14 may also be positioned in direct contact with an epicardial or endocardial surface of an atrium or other structure of the heart. Positioning the load detection assembly 14 in direct contact with a surface of the heart 12 enables direct measurement of the motion of the surface. Alternatively, the load detection assembly 14 may not be positioned in direct contact with a surface of the heart 12, but rather may be positioned in direct contact with other bodily tissue (e.g., the pericardial sac) that is adjacent to, or in direct contact with, a surface of the heart 12.

The load detection assembly 14 may also be positioned to indirectly measure the motion of the heart by measuring other properties that relate to, and can be used to determine, pressure. For example, the load detection assembly 14 can be positioned within the heart 12 in direct contact with a flow path of blood through the heart 12. Pressure information about the heart 12 can then be determined based on the motion of blood through the heart. One example of measuring blood flow includes positioning the load detection assembly 14 within a ventricle (e.g., the left ventricle) of the heart 12 in direct contact with blood flowing through the ventricle to measure blood flow therethrough. The load detection assembly 14 may also be positioned on, adjacent, and/or within vessels leading into and out of the heart 12 to obtain pressure information about the heart 12.

The position of the load detection assembly 14 may be selected anywhere within, on, and/or adjacent the heart 12 to determine pressure information of the heart 12 overall and/or at specific locations adjacent the load detection assembly 14. In some embodiments, to provide more comprehensive pressure information, a plurality of load detection assemblies 14 (whether part of the same lead or whether connected to the same processing unit 18) may be positioned at different locations within, on, and/or adjacent the heart 12 and/or at different orientations with respect to other load detection assemblies 14. For example, because motion of the heart 12 is generally not linear, it may be desirable to position a pair of load detection assemblies 14 oriented about orthogonally to each other such that the pair of load detection assemblies 14 each detect forces in a direction arranged about perpendicularly to each other (e.g., for measuring both short and long axis motion of heart 12).

Generally, the pressure of the heart 12 is assessed using the sensor system 10 for diagnosis and/or treatment of the patient. In addition to being useful for generally monitoring the progression of a patient's cardiac disease, pressure of the heart 12 may be monitored over time to monitor the patient's response to therapy and make any appropriate changes thereto. For example, the pressure information obtained by the sensor system 10 may provide a physician with information as to whether the hemodynamic functioning of a patient has improved, how scar formation is progressing, the status of local or global heart failure, and/or the like. The pressure information may also be used in combination with other systems to control functions of such other systems. For example, the pressure information may be used by, but is not limited to being used by another system (not shown), such as, but not limited to, a pulse generator, a pacemaker, an implantable cardioverter defibrillator, a defibrillator, a therapy delivery module that paces and/or provides electrical stimulation to the heart 12, and/or the like to, for example, control an appropriate pacing scheme or defibrillation event. External systems (not shown), such as, but not limited to, an external health monitoring system at a treatment facility and/or the patient's home may also make use of the pressure information for treatment and/or diagnosis purposes.

Voltage measurement signals from the load detection assembly 14 are provided to the processing unit 18 via an electrical connection therebetween. The load detection assembly 14 may be electrically connected to the processing unit 18 through the lead 16, as is shown in FIG. 1. Optionally, the load detection assembly 14 may be incorporated into the lead of another system (not shown), such as, but not limited to a pulse generator, a pacemaker, an implantable cardioverter defibrillator, a defibrillator, a therapy delivery module that paces and/or provides electrical stimulation to the heart 12, and/or the like. Additionally or alternatively to a lead, the load detection assembly 14 may be electrically connected to the processing unit 18 using a wireless connection, such as, but not limited to, using an RF transmitter (not shown in FIG. 1) electrically connected to the load detection assembly 14.

The processing unit 18 processes the voltage measurement signals received from the load detection assembly 14 to determine the force represented by each of the signals. The processing unit 18 may further process the force to determine pressure information of the heart 12 or portions thereof. The processing unit 18 may include a memory (not shown) for storing the voltage measurement signals received from the load detection assembly 14, as well as for storing any determined pressures, any determined pressure information, and/or other information relevant to treatment and/or diagnosis of the patient. The processing unit 18 communicates with an external system 40, such as, but not limited to, an external health monitoring system at a treatment facility and/or the patient's home, and/or a laptop, handheld, or desktop computer at the treatment facility. The processing unit 18 may communicate any determined pressure information or other relevant information to the external system 40 for use by the external system 40 and/or a physician in diagnosing, treating, and/or monitoring the patient. Additionally or alternatively, the external system 40 may determine pressure information of the heart by processing voltage measurement signals, any determined forces, and/or other relevant information received from the processing unit 18. The processing unit 18 may communicate with the external system 40 using a wireless connection (as shown in FIG. 1) and/or a wired connection. The processing unit 18 may also cooperate with other systems implanted within the patient's body to make use of the pressure information obtained by the sensor system 10, as is described above. For example, the processing unit 18 may optionally communicate with, constitute the processing unit of, or be incorporated into another system (not shown) implanted within the patient's body, such as, but not limited to a pulse generator, a pacemaker, an implantable cardioverter defibrillator, a defibrillator, a therapy delivery module that paces and/or provides electrical stimulation to the heart 12, and/or the like.

Figure 2:
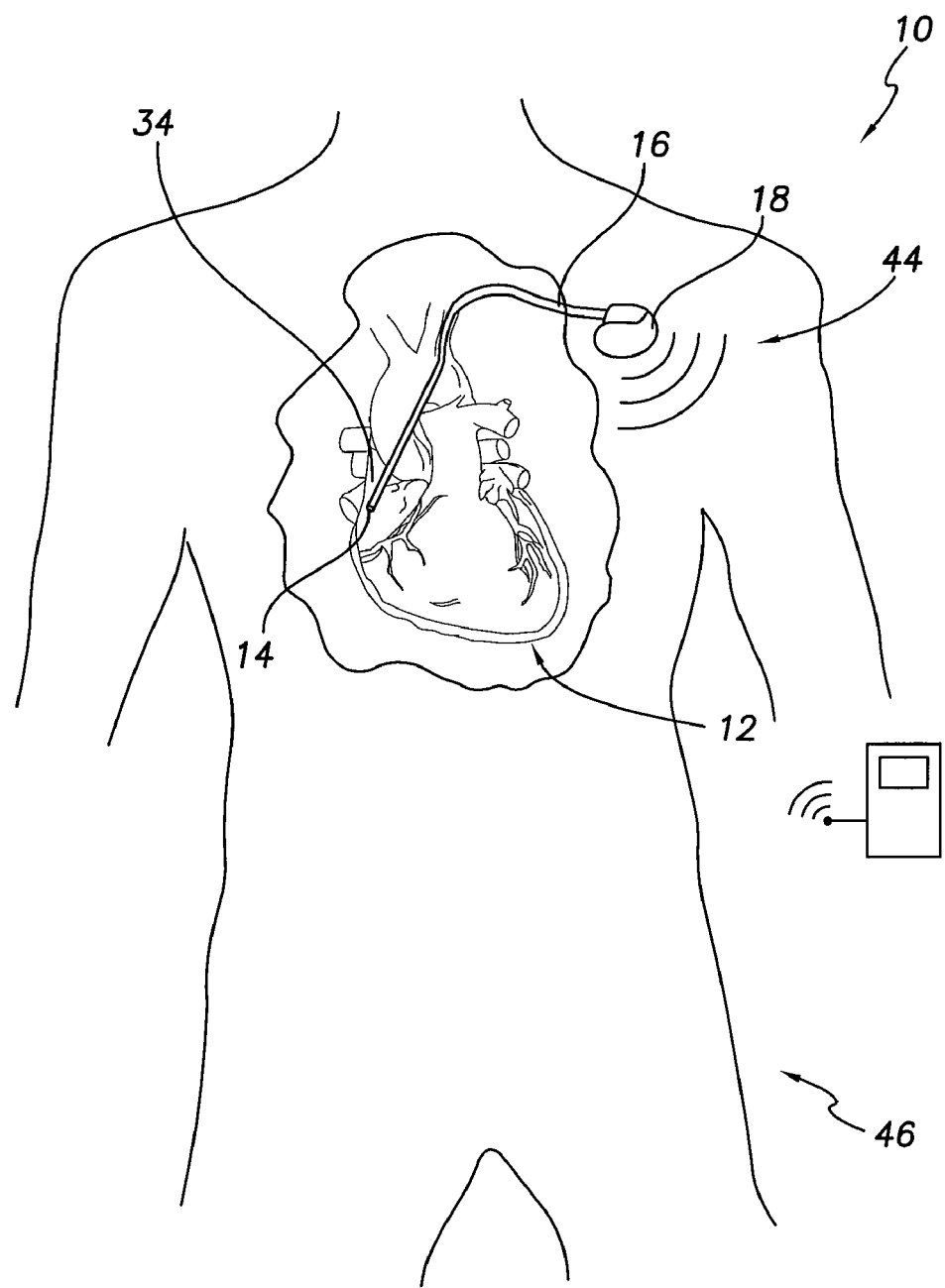
FIG. 2 illustrates an implantable sensor system formed in accordance with an alternative embodiment.

The processing unit 18 may be implanted at any suitable location within the body that enables it to function as described herein, such as, but not limited to, in the abdomen 42 (as shown in FIG. 1) or a chest region 44 (as shown in FIG. 2). Alternatively, the processing unit 18 may be positioned externally to the patient's body. For example, the processing unit 18 may be worn externally on the patient's hip 46 or another body portion, or may remain at a treatment facility and be connected (e.g., via a lead or wirelessly) to the load detection assembly 14 when the patient comes to the facility for treatment.

FIG. 2 illustrates the sensor system 10 formed in accordance with an alternative embodiment. Specifically, as shown in FIG. 2, the distal end portion 22 of the lead 16 is placed inside the heart 12. The load detection assembly 14 is positioned at the distal end portion 22, as opposed to remote from the distal end portion 22 as is illustrated in FIG. 1. Optionally, a portion of the load detection assembly 14 may extend beyond the distal end portion 22 of the lead 16 such that the load detection assembly 14 is exposed to the environment surrounding the distal end portion 22. In an exemplary embodiment, the load detection assembly 14 is positioned in direct contact with the endocardial surface 34 of the heart 12, as opposed to the epicardial surface 32 as shown in FIG. 1. Further, the processing unit 18 is positioned within the chest region 44 of the patient.

Figure 3:
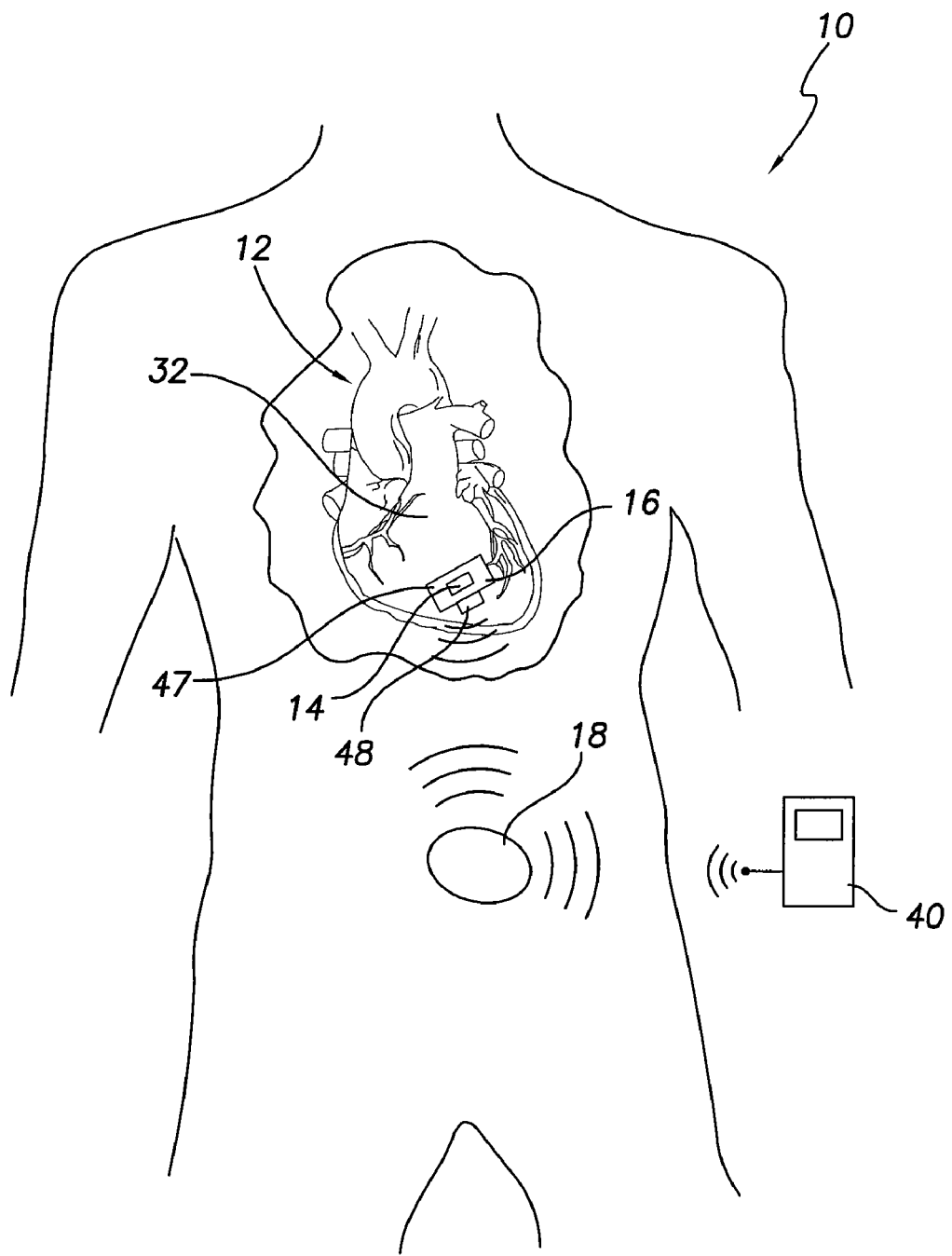
FIG. 3 illustrates an implantable sensor system formed in accordance with an alternative embodiment.

FIG. 3 illustrates the sensor system 10 formed in accordance with another alternative embodiment. Specifically, as shown in FIG. 3, the load detection assembly 14 is positioned in direct contact with the epicardial surface 32, similar to the load detection assembly 14 shown in FIG. 1. The load detection assembly 14 is anchored to the heart using an attachment device 16 other than an implantable lead. For example, in the illustrated embodiment, the attachment device 16 constitutes a patch 47 that is adhered to the surface of the heart 12. The load detection assembly 14 is electrically connected to the processing unit 18 using a radio-frequency (RF) transmitter 48 electrically connected to the load detection assembly 14, as opposed to the lead 16 (FIG. 1).

Figure 4:
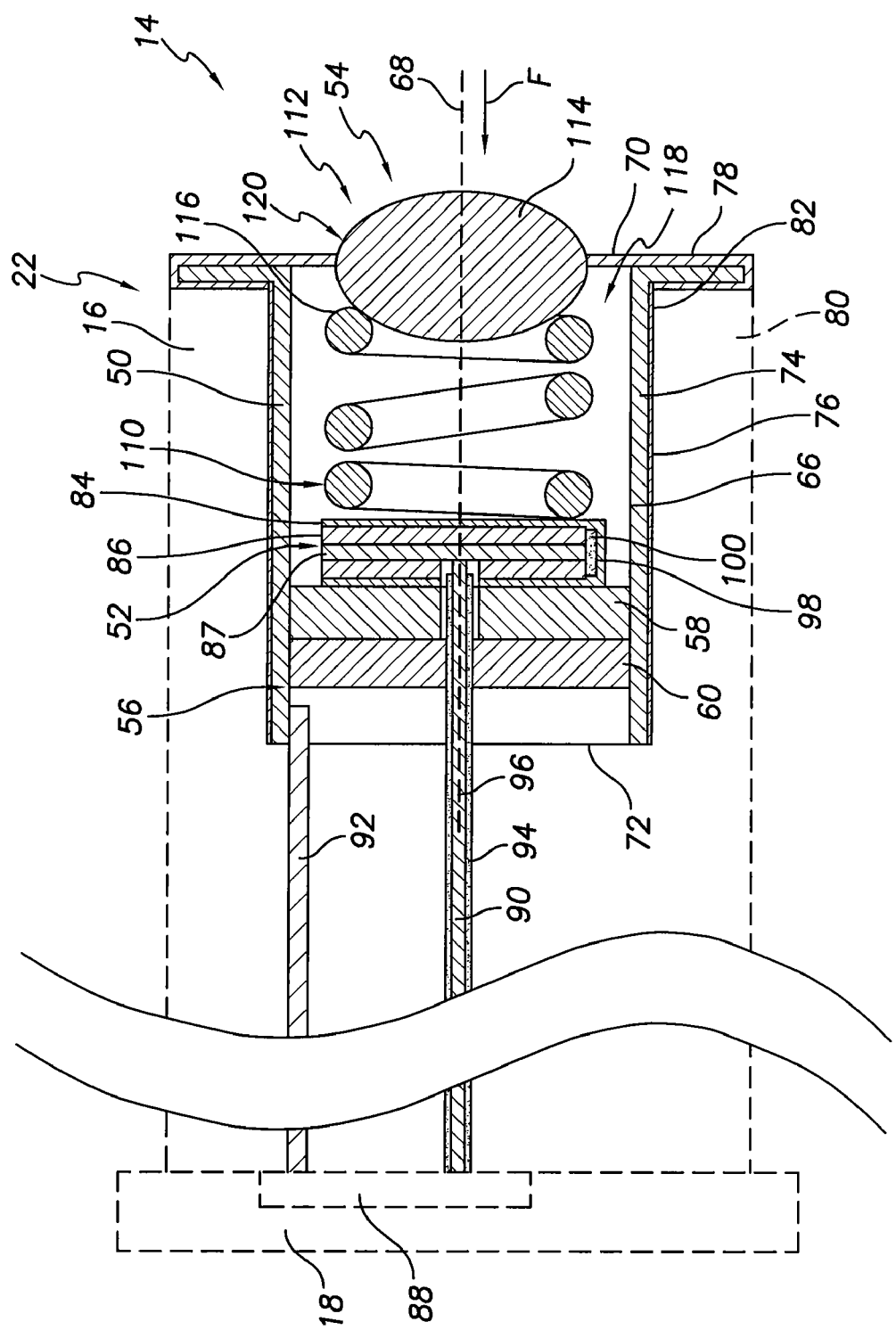
FIG. 4 illustrates a load detection assembly for the implantable sensor systems shown in FIGS. 1-3 and formed in accordance with an exemplary embodiment.

FIG. 4 illustrates the load detection assembly 14 formed in accordance with an exemplary embodiment. The load detection assembly 14 includes a housing 50 that holds a sensor 52 and a load transfer element 54. The load transfer element 54 engages the sensor 52 and conveys a force induced on the load transfer element 54 from the surrounding environment to the sensor 52.

In an exemplary embodiment, a support 56 is provided within the housing 50. The sensor 52 is coupled to the support 56 such that the sensor 52 is rigidly positioned within the housing 50. As such, the only forces imparted on the sensor 52 are the forces from the load transfer element 54. The support 56 includes a conductive portion 58 and a non-conductive portion 60. As will be explained in more detail below, the sensor 52 is coupled to the conductive portion 58, which is also coupled to the housing 50. As such, a conductive path is created between the sensor 52 and the housing 50. The conductive path is used to transmit the voltage measurement signals to the processing unit 18, as will be explained in more detail below. The conductive portion 58 is fabricated from a conductive material such as a metal or metal alloy that is bio-compatible. Exemplary materials for the conductive portion 58 include a platinum/iridium (Pt—Ir) alloy, a nickel/titanium (Ni—Ti) alloy, an MP35N® alloy, and the like. The non-conductive portion 60 is fabricated from a non-conductive material such as a bio-compatible polymer, epoxy, or a similar type of material. The non-conductive portion 60 is rigidly attached to the housing 50 to provide a rigid base for the sensor 52.

The housing 50 includes a generally hollow shell 66 extending along a longitudinal axis 68 between an exposed end 70 and an embedded end 72. The embedded end 72 is received within and surrounded by the lead 16, whereas the exposed end 70 is generally exposed to the bodily tissue and/or bodily fluid of an environment surrounding the lead 16. In the illustrated embodiment, the housing 50 is generally cylindrical about the longitudinal axis 68, however, other shaped housings 50 may be used in alternative embodiments. Optionally, the shell 66 may include an inner layer 74 and an outer layer 76. The inner layer 74 is fabricated from a conductive material such as a metal or metal alloy that is bio-compatible. Exemplary materials for the inner layer include a Pt—Ir alloy, a Ni—Ti alloy, an MP35N® alloy, and the like. The outer layer 76 is fabricated from a non-conductive or dielectric material that is bio-compatible, such as a polymer. Optionally, the outer layer 76 may include a coating fabricated from a noble metal.

In an exemplary embodiment, the exposed end 70 includes a flange 78 which may be used to attach the load detection assembly 14 to the lead 16. For example, the housing 50 may be securely attached to the lead 16 by an interference fit between the insulating sheath 80 of the lead 16 and an outer surface 82 of the housing 50. The flange 78 is used to control the depth of insertion of the housing 50 within the lead 16, thereby ensuring that the exposed end 70 remains exposed to the surrounding environment. For example, the housing 50 may be inserted into the lead 16 until the flange 78 abuts the insulating sheath 80. As described above, the housing 50 may be attached to lead 16 at the distal end portion 22, such as illustrated in FIG. 2. Alternatively, the housing 50 may be inserted through a side portion of the insulating sheath 80 and attached thereto, such as illustrated in FIG. 1. In the illustrated embodiment of FIG. 4, the housing 50 is shown inserted into the distal end portion 22 of the lead 16, which is shown in phantom in FIG. 4.

The sensor 52 is adapted to detect a force imposed upon, and transferred by, the load transfer element 54 from the surrounding environment to a transfer surface 84 of the sensor 52. The force is indicated generally by the arrow F which acts in a predetermined single direction. For example, in the illustrated embodiment, the load transfer element 54 transfers forces longitudinally to the sensor 52. The longitudinal forces are generally transferred by the load transfer element 54 perpendicular to the transfer surface 84 of the sensor 52. The sensor 52 generates a charge when a force is applied to a surface of the sensor 52.

In an exemplary embodiment, the sensor 52 includes a piezoelectric sensor fabricated from a material having piezoelectric properties, which may include a polymer material. The piezoelectric sensor 52 generates a charge when a force is applied to the piezoelectric sensor 52 according to the following relations:

$$Q = d \cdot F \text{ or } Q = d \cdot P \cdot A_{fp} \quad (1)$$

In the above equations, Q is the charge, F is the applied force, d is the piezoelectric charge coefficient, P is the pressure and $A_{fp}$ is the footprint area on which the force is acting. In one embodiment, the sensor 52 has a disk shaped footprint area. Other shaped footprint areas are possible in alternative embodiments. Because piezoelectric materials can be sensitive to deflections on a relatively small scale and can be sensitive to small loads, the piezoelectric sensor 52 is adapted for pressure detection of bodily tissue and/or bodily fluids. However, the piezoelectric sensor 52 may be adapted for different applications based on the piezoelectric material used and the size of the sensor 52.

In an exemplary embodiment, the piezoelectric sensor 52 includes multiple piezoelectric elements 86 arranged in a layered or stacked configuration. The piezoelectric elements 86 are arranged in-line with one another along a common axis. Optionally, the common axis may be coincident with the longitudinal axis 68 of the load detection assembly 14. The piezoelectric elements 86 may be stacked directly on, and abut, one another such that adjacent piezoelectric elements 86 have mating surfaces of the same polarity, as indicated by the + and − signs in FIG. 4. Alternatively, and as illustrated in FIG. 4, the piezoelectric elements 86 may be stacked on one another with a conductive element 87, such as a wire or a film, positioned between the piezoelectric elements 86. By arranging the piezoelectric elements 86 in a stacked configuration, each of the piezoelectric elements 86 cooperate with one another such that a force induced onto one of the piezoelectric elements 86 (e.g. the piezoelectric element engaged with the load transfer element 54) is experienced by each of the piezoelectric elements 86. The charge potential of the piezoelectric sensor 52 is increased by providing multiple layers of piezoelectric elements 86 because the charge produced by the piezoelectric elements 86 is cumulative. In an exemplary embodiment, the charge output of the sensor 52 may be determined according to the following relation:

$$Q = n \cdot d \cdot F \text{ or } Q = n \cdot d \cdot P \cdot A_{fp} \quad (2)$$

In the above equations, n is the number of layers of piezoelectric elements 86. The voltage output of the sensor 52 may be determined according to the following relation:

$$V = Q/C \quad (3)$$

In the above equation, V is the voltage and C is the capacitance of the piezoelectric sensor 52. The measured voltage V is used by the processing unit 18 to determine the pressure sensed by the load detection assembly 14. Optionally, an amplifier 88, such as a charge amplifier, may be electrically connected to the sensor 52. The amplifier 88 may amplify the charge or the voltage generated by the load detection assembly 14. The amplifier 88 may be coupled to the processing unit 18, to the load detection assembly 14, or to the lead 16 at a location between the processing unit 18 and the load detection assembly 14.

In an exemplary embodiment, the load detection assembly 14 is electrically connected to the processing unit 18 by a first conductor 90 and a second conductor 92. The voltage generated by the piezoelectric sensor 52 is transmitted along the conductors 90 and 92. In an exemplary embodiment, the first conductor 90 is connected to the conductive element 87, such as by a soldered connection, a conductive adhesive connection, and the like. However, the first conductor 90 may be directly connected to at least one of the piezoelectric elements 86 in alternative embodiments. The first conductor 90 may have an insulative sheath 94 that surrounds a conductive element 96 for isolating the first conductor 90 from directly contacting the piezoelectric elements, the load detection assembly 14 and/or various structures of the lead 16. The conductive element 96 may be fabricated from a metal, a metal alloy, a conductive ceramic, and the like.

The second conductor 92 is electrically connected to at least one of the other piezoelectric elements 86. In the illustrated embodiment, the second conductor 92 is electrically connected to the outer surfaces (e.g. the positive surfaces) of the piezoelectric elements 86 via the conductive inner layer 74 of the shell 66 and the conductive portion 58 of the support 56. The second conductor 92 may be connected to the inner layer 74 via a soldered connection, a conductive adhesive connection, and the like. Optionally, when multiple piezoelectric elements 86 are provided, every other one of the piezoelectric elements 86 are coupled to one another. In the illustrated embodiment, a casing 98 is provided to interconnect respective ones, and/or respective surfaces, of the piezoelectric elements 86. An insulator 100 may be provided between the casing 98 and portions of the piezoelectric elements 86. The casing 98 is electrically connected to the conductive portion 58 of the support 56, and thus to the second conductor 92.

The load transfer element 54 includes a first end 110 that directly engages the sensor 52 and a second end 112 that is exposed to the environment surrounding the housing 50. In an exemplary embodiment, the load transfer element 54 includes a plunger 114 at the second end 112 that is exposed beyond the exposed end 70 of the housing 50. The plunger 114 engages the bodily tissue and/or the bodily fluids being monitored by the load detection assembly 14. The load transfer element 54 also includes a spring element 116 extending between the plunger 114 and the sensor 52. The spring element 116 transfers forces imposed on the plunger 114 to the sensor 52. In an exemplary embodiment, the spring element 116 transfers forces to the sensor 52 in a single direction extending parallel to the longitudinal axis 68.

In use, the lead 16 is attached to the heart 12 (shown in FIGS. 1-3) such that the load detection assembly 14 is exposed to the tissues and/or fluids of interest. The plunger 114 engages the tissues and/or fluids such that movement of the tissues and/or fluids are transferred by the load transfer element 54 to the sensor 52. The housing 50 isolates the sensor 52 from forces other than the force imposed on the sensor 52 by the load transfer element 54. For example, the housing 50 may isolate the sensor 52 from lateral, shear, rotational or bending forces. Additionally, the support 56 is provides to isolate the sensor 52 from any forces imposed by movement of the lead 16, such as bending forces of the lead 16. As such, only the forces transferred to the sensor 52 by the load transfer element 54 are detected by the sensor 52. As a result, a more reliable signal having reduced noise may be obtained. Optionally, the first conductor 90 may be securely attached to the support such that movement of the conductor within the lead 16 is isolated from the sensor 52.

In an exemplary embodiment, the housing 50 defines an interior chamber 118 that receives and isolates the sensor 52. The interior chamber 118 is accessed from the surrounding environment via an opening 120 at the exposed end 70. In the illustrated embodiment, the load detection assembly 14 is positioned at the distal end portion 22 of the lead 16 such that the opening 120 extends generally perpendicular to the longitudinal axis of the lead 16. In alternative embodiments, the opening 120 may extend generally parallel to the longitudinal axis of the lead 16. Optionally, the plunger 114 may be seated against, and close, the opening 120. The interior chamber 118 may be sealed from the surrounding environment by the plunger or by an additional seal (not shown).

Figure 5:
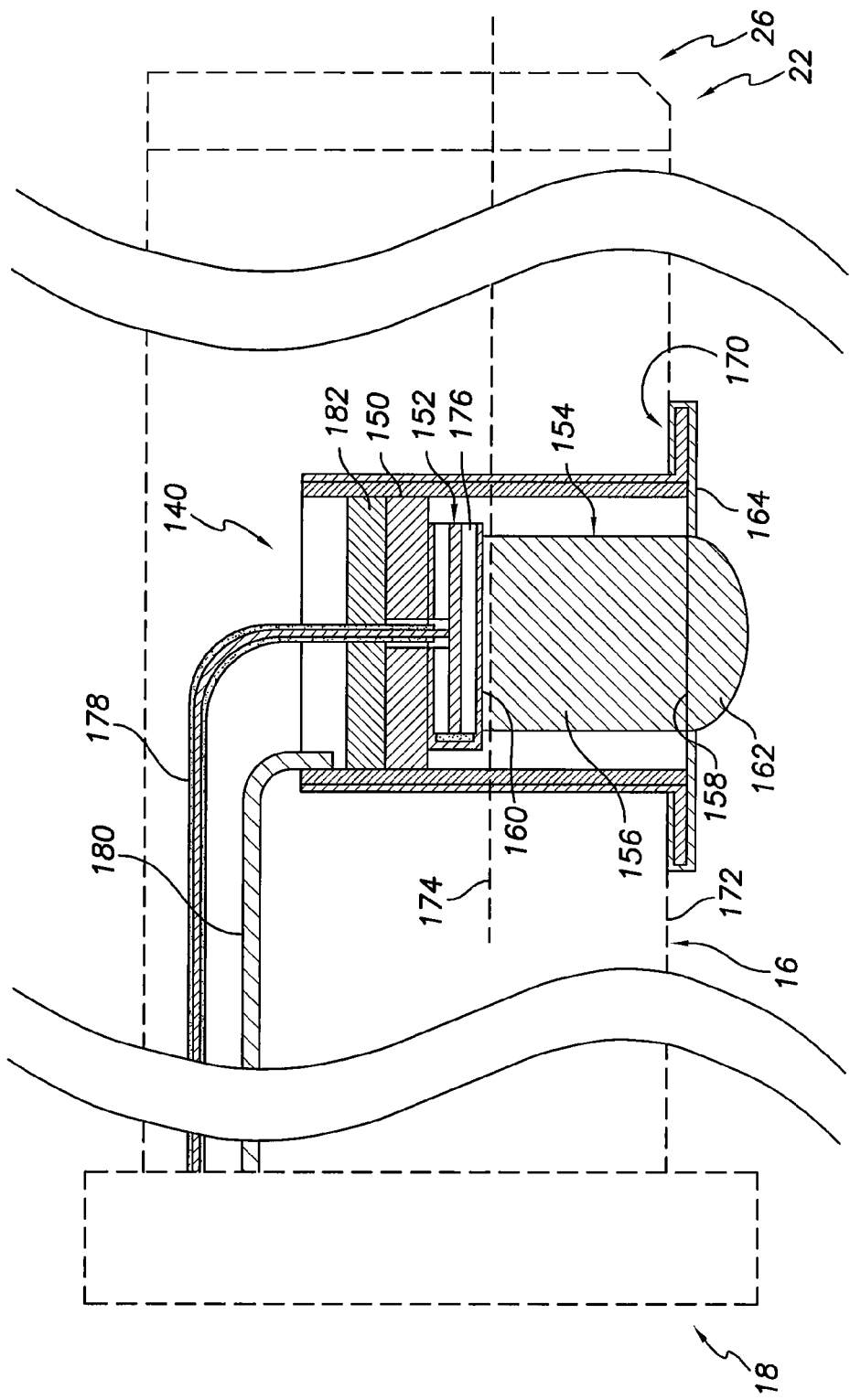
FIG. 5 illustrates an alternative load detection assembly formed in accordance with an alternative embodiment.

FIG. 5 illustrates an alternative load detection assembly 140 formed in accordance with an alternative embodiment. The load detection assembly 140 includes a housing 150 that holds a sensor 152 and a load transfer element 154. The housing 150 and the sensor 152 are similar to the housing 50 and the sensor 52 described above with reference to FIG. 4. The load transfer element 154 engages the sensor 152 and conveys a force induced on the load transfer element 154 from the surrounding environment to the sensor 152.

In contrast to the load transfer element 54 that utilizes a spring to transfer the force to the sensor 52, the load transfer element 154 includes a transfer body 156. The transfer body 156 extends between a first end 158 that directly engages the sensor 152 and a second end 160 that is exposed to the environment surrounding the housing 150. In an exemplary embodiment, the load transfer element 154 includes a plunger 162 at the second end 160 that is exposed beyond an exposed end 164 of the housing 150. Optionally, the plunger 162 may be unitarily formed with the transfer body 156. The plunger 162 engages the bodily tissue and/or the bodily fluids being monitored by the load detection assembly 140. As the plunger 162 is deflected, or otherwise forced inward, the transfer body 156 transfers a corresponding force to the sensor 152. In an exemplary embodiment, the transfer body 156 and the plunger 162 are both fabricated from a solid bio-compatible, polymer-based material. In an alternative embodiment, only an outer shell of the transfer body 156 and/or the plunger 162 are fabricated from a solid material, and the inner portion of the outer shell is filled with a fluid or a gel which operates to transfer the forces from the plunger 162 to the sensor 152.

In the illustrated embodiment, the load detection assembly 140 is coupled to the lead 16 remote from the distal end portion 22. A tip electrode 26 is attached to the distal end portion 22. The load detection assembly 140 is received within an opening 170 extending through a side 172 of the lead body 20. The side 172 and the opening 170 each extend parallel to a longitudinal axis 174 of the lead 16.

In use, the lead 16 is attached to a surface of the heart, such as the epicardial surface 32 (shown in FIG. 1), in a manner similar to the attachment illustrated in FIG. 1. The load detection assembly 140 is adapted for monitoring the heart tissue that the lead 16 overlays. Optionally, the lead 16 may be positioned within the pericardial sac and the load detection assembly 140 may detect physiological characteristics of the pericardial sac. The forces detected by the load detection assembly 140 are transferred by the load transfer element 154 to the sensor 152 in a direction that is perpendicular to the longitudinal axis 174 of the lead 16. In an exemplary embodiment, the sensor 152 includes piezoelectric elements 176 that create a charge when the force is imposed on the transfer surface thereof by the load transfer element 154. The sensor 152 is electrically connected to first and second conductors 178 and 180 that transmit voltage measurement signals from the sensor 152 to the processing unit 18. Optionally, the first and/or the second conductors 178, 180 may have an insulative sheath for insulating the conductors 178, 180. The sensor 152 is isolated from secondary forces, such as shear forces, lateral forces, bending forces, rotational forces and the like, by the housing 150 and a support 182. The support 182 also operates to isolate the sensor 150 from forces induced by the first and or second conductors 178, 180.

Figure 6:
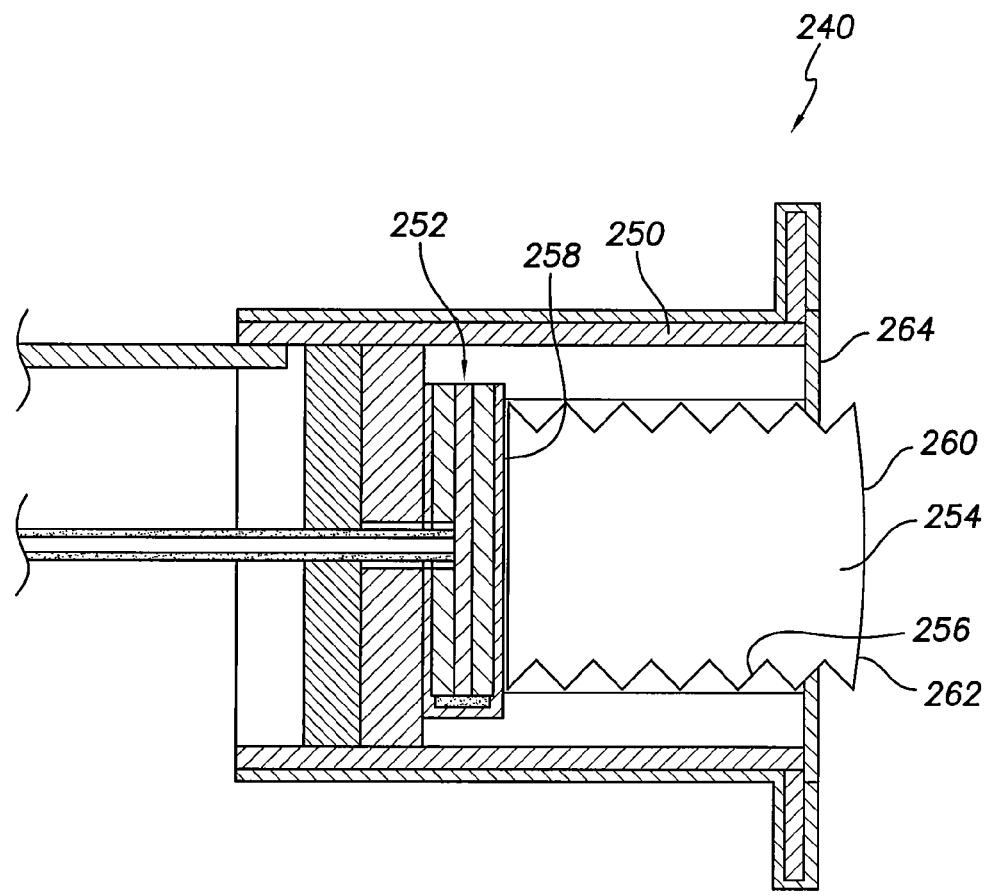
FIG. 6 illustrates another alternative load detection assembly.

FIG. 6 illustrates another alternative load detection assembly 240 formed in accordance with an alternative embodiment. The load detection assembly 240 includes a housing 250 that holds a sensor 252 and a load transfer element 254. The housing 250 and the sensor 252 are similar to the housing 50 and the sensor 52 described above with reference to FIG. 4. The load transfer element 254 engages the sensor 252 and conveys a force induced on the load transfer element 254 from the surrounding environment to the sensor 252.

In contrast to the load transfer element 54 that utilizes a spring to transfer the force to the sensor 52, or the load transfer element 154 that utilizes a solid or liquid filled transfer body 156 (shown in FIG. 5), the load transfer element 254 includes a bellows 256 to transfer forces to the sensor 252. The bellows 256 extends between a first end 258 that directly engages the sensor 252 and a second end 260 that is exposed to the environment surrounding the housing 250. In an exemplary embodiment, the load transfer element 254 includes a diaphragm 262 at the second end 260 that is exposed beyond an exposed end 264 of the housing 250. The diaphragm 262 engages the bodily tissue and/or bodily fluid and the load is transferred by the bellows 256.

Exemplary embodiments are described and/or illustrated herein in detail. The embodiments are not limited to the specific embodiments described herein, but rather, components and/or steps of each embodiment may be utilized independently and separately from other components and/or steps described herein. Each component, and/or each step of one embodiment, can also be used in combination with other components and/or steps of other embodiments. For example, although specific sensor elements are described and/or illustrated with specific attachment devices, each described and/or illustrated sensor element may be used with any of the described and/or illustrated attachment devices as is appropriate. When introducing elements/components/etc. described and/or illustrated herein, the articles "a", "an", "the", "said", and "at least one" are intended to mean that there are one or more of the element(s)/component(s)/etc. The terms "comprising", "including" and "having" are intended to be inclusive and mean that there may be additional element(s)/component(s)/etc. other than the listed element(s)/component(s)/etc. Moreover, the terms "first," "second," and "third," etc. in the claims are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

While the invention has been described in terms of various specific embodiments, those skilled in the art will recognize that the invention can be practiced with modification within the spirit and scope of the claims.

What is claimed is:

1. An implantable lead, comprising:
   a lead body, having a distal end and a proximal end, configured to be implanted in a patient;
   a connector provided at the proximal end; and
   a load detection assembly provided on the lead body at the distal end, the load detection assembly comprising a housing that holds a sensor and a load transfer element, the load transfer element engaging the sensor and conveying a force induced on the load transfer element to the sensor;
   wherein the sensor comprises multiple sensors linearly stacked on one another along a longitudinal axis of the lead body, and aligned to be responsive to an incident force directed parallel to the longitudinal axis onto one of the sensors; and
   wherein the multiple sensors comprise multiple piezoelectric sensors stacked on one another such that adjacent piezoelectric sensors have mating surfaces of the same polarity.

2. An implantable lead in accordance with claim 1, wherein the load transfer element only conveys, to the sensor, longitudinal forces that are directed perpendicular to a surface of the sensor.

3. An implantable lead in accordance with claim 1, wherein the load transfer element has a first end that directly engages a surface of the sensor and a second end that is exposed to a surrounding environment.

4. An implantable lead in accordance with claim 1, wherein the housing is positioned at the distal end of the lead body, the load transfer element has an exposed end that is exposed to a surrounding environment of the distal end.

5. An implantable lead in accordance with claim 1, wherein the housing is positioned remote from the distal end of the lead body, the load transfer element has an exposed end that is exposed to a surrounding environment adjacent the lead body.

6. An implantable lead in accordance with claim 1, wherein the housing includes an interior chamber that holds the sensor and load transfer element, the interior chamber being exposed through an opening in the housing to incident forces of a surrounding environment directed perpendicular to the opening.

7. An implantable lead in accordance with claim 1, wherein the housing includes an interior chamber that holds the sensor and load transfer element, the interior chamber being exposed through an opening in the housing extending perpendicular to a longitudinal axis of the lead body.

8. An implantable lead in accordance with claim 1, wherein the housing includes an interior chamber that holds the sensor and load transfer element, the interior chamber having an opening in the housing extending parallel to a longitudinal axis of the lead body.

9. An implantable lead in accordance with claim 1, wherein the load detection assembly includes a support, the sensor being coupled to the support to rigidly retain the sensor within the housing.

10. An implantable lead in accordance with claim 1, wherein the load detection assembly includes a support, the support being positioned at a proximal end of the sensor.

11. An implantable lead in accordance with claim 1, wherein the load transfer element comprises at least one of a spring, a deflectable solid polymer, a gel and a liquid filled pouch.

12. An implantable lead, comprising:
    a lead body, having a distal end and a proximal end, configured to be implanted in a patient;
    a connector provided at the proximal end; and
    a load detection assembly provided on the lead body at the distal end, the load detection assembly including multiple piezoelectric sensors arranged in-line with one another along a common longitudinal axis of the lead body, the piezoelectric sensors cooperating with one another such that a force induced onto one of the piezoelectric sensors is experienced by the other piezoelectric sensors;
    wherein the piezoelectric sensors are stacked on one another such that adjacent piezoelectric sensors have mating surfaces of the same polarity.

13. An implantable lead in accordance with claim 12, wherein each of the piezoelectric sensors having opposed surfaces that are arranged perpendicular to the longitudinal axis.

14. An implantable lead in accordance with claim 12, wherein the piezoelectric sensors are stacked directly on, and abut against, one another.

15. An implantable lead in accordance with claim 12, wherein the piezoelectric sensors are aligned to be responsive to an incident force directed parallel to the longitudinal axis onto one of the piezoelectric sensors.

* * * * *